United States Patent [19]

Kempf et al.

[11] 4,247,640
[45] Jan. 27, 1981

[54] FERMENTATION PROCESS FOR 6-HYDROXYMETHYL-2-(2-AMINOETHYL-THIO)-1-CARBADETHIAPEN-2-EM-3-CARBOXYLIC ACID

[75] Inventors: August J. Kempf, Staten Island, N.Y.; Kenneth E. Wilson, Westfield, N.J.

[73] Assignee: Merck & Co., Inc., Rahway, N.J.

[21] Appl. No.: 59,811

[22] Filed: Jul. 23, 1979

[51] Int. Cl.³ .............................................. C12P 17/18
[52] U.S. Cl. ..................................... 435/119; 435/886
[58] Field of Search ................................. 435/121, 119

[56] References Cited

U.S. PATENT DOCUMENTS 3,950,357  4/1976  Kahan et al. ........................... 435/121

Primary Examiner—Alvin E. Tanenholtz
Attorney, Agent, or Firm—James A. Arno; Julian S. Levitt

[57] ABSTRACT

Disclosed is a fermentation process for producing and isolating 6-hydroxymethyl-2-(2-aminoethylthio)-1-carbadethiapen-2-em-3-carboxylic acid (I) which is useful as an antibiotic:

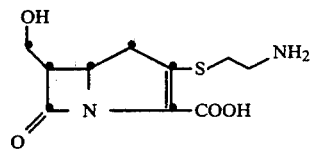

2 Claims, No Drawings

FERMENTATION PROCESS FOR 6-HYDROXYMETHYL-2-(2-AMINOETHYLTHIO)-1-CARBADETHIAPEN-2-EM-3-CARBOXYLIC ACID

BACKGROUND OF THE INVENTION

This invention relates to a fermentation process for preparing 6-hydroxymethyl-2-(2-aminoethylthio)-1-carbadethiapen-2-em-3-carboxylic acid (I) which is useful as an antibiotic:

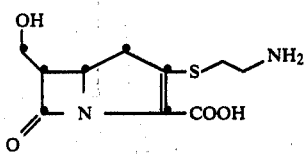
I

The antibiotic of Structure I will be recognized as "northienamycin". Thienamycin (II) is disclosed and claimed in U.S. Pat. No. 3,950,357 (Apr. 13, 1976):

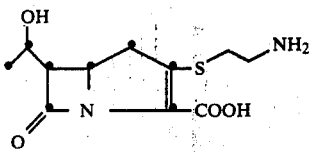
II

This patent disclosing and claiming thienamycin is incorporated herein by reference since northienamycin (I) is isolated from the very same fermentation broths that yield thienamycin.

The compound of Structure I is fully disclosed and claimed in co-pending, commonly assigned U.S. Pat. Application Ser. No. 933,681 (filed Aug. 17, 1978). To the extent that the cited co-pending, commonly assigned U.S. Patent Application Ser. No. 933,681 describes the antibiotic utility of I, it is incorporated herein by reference.

DETAILED DESCRIPTION OF THE INVENTION

Incorporated by reference U.S. Pat. No. 3,950,357 fully describes the fermentation procedures involving the novel microorganism *Streptomyces cattleya*. It is from these fermentation broths that the compound of Structure I was unexpectedly found. The following example describes the basic fermentation process and the isolation procedures utilized in isolating the antibiotic I in substantially pure form.

EXAMPLE 1

A tube of lyophilized culture of *Streptomyces cattleya* is opened aseptically and the contents suspended in 50 ml of sterile Medium A contained in a 250 ml baffled Erlenmeyer flask. Medium A has the following composition:

| Medium A | |
|---|---|
| Yeast Autolysate (Ardamine *) | 10.0 g |
| Glucose | 10.0 g |
| Phosphate Buffer* | 2.0 ml |
| MgSO$_4$7H$_2$O | 0.05 g |
| Distilled H$_2$O | 1000 ml |
| pH: adjust to 6.5 using NaOH | |

| | |
|---|---|
| * Ardamine: Yeast Products Corporation | |
| ** Phosphate Buffer Solution | |
| KH$_2$PO$_4$ | 91.0 g |
| NaHPO$_4$ | 95.0 g |
| Distilled H$_2$O | 1000 ml |

The inoculated flask is shaken at 28° C. on a 220 rpm shaker (2 inches throw) for 48 hours. A portion (40 ml.) of the 48-hour broth is removed aseptically and mixed with 40 ml. of aqueous, sterile 20% (v/v) glycerol. Aliquout quantities (2.0 ml.) of the resulting mixture are pipetted into sterile 1 dram vials which are then frozen and stored in the vapor phase of a liquid nitrogen freezer.

Frozen vial contents are used to inoculate a 250 ml. baffled Erlenmeyer flask containing 50 ml. of Medium A. This seed flask is shaken at 28° C. on a 160 rpm shaker at 28° C. for 24 hours.

Portions (10.0 ml.) from this seed flask are used to inoculate 2 liter baffled Erlenmeyer flasks containing 500 ml. of Medium A. These seed flasks are shaken on a 160 rpm shaker at 28° C. for 24 hours.

A portion (1.0 l.) of the pooled contents of these seed flasks is used to inoculate a 756 liter stainless steel fermentor containing 467 liters of Medium A. This tank is operated at 28° C. using an agitation rate of 130 rpm and an airflow of 10 cu. ft. per minute for 24 hours. Polyglycol 2000 (Dow Chemical Corp.) is used as required as a defoamer but not to exceed 0.1%. Measurements of pH and dextrose are made and are as follows:

| | Age (Hours) | | |
|---|---|---|---|
| | 0 | 12 | 14 |
| pH | 6.4 | 6.4 | 6.6 |
| Dextrose mg/ml | 8.1 | 8.1 | 8.1 |

A portion (453 l.) of this growth are used to inoculate a 5670 liter stainless steel fermentor containing 4082 liters of Medium E, wherein Medium E has the composition:

| Medium E | |
|---|---|
| Cerelose | 25.0 g |
| Corn Steep Liquor (wet basis) | 15.0 g |
| Distiller's Solubles | 10.0 g |
| Cottonseed Media (pharmamedia) | 5.0 g |
| CoCl$_2$ . 6H$_2$O | 0.01 g |
| CaCO$_3$ (after pH adjustment) | 3.0 g |
| Polyglycol 2000 | 0.25% |
| Tap water | 1000 ml |
| pH: adjust to 7.3 using NaOH | |

This tank is operated at 24° C. using an agitation rate of 70 rpm and an airflow of 54.3 cu.ft. per minute for 144 hours. Defoamer, polyglycol 2000, is added as required but does not exceed 0.1%. Assays are performed using the supernatent of centrifuged broth. The results are tabulated in the table below under the heading "Antibiotic Activity vs ATCC 6538P". Assays are also run by the dis-diffusion procedure using ⅜-inch filter-paper discs and 10 ml. assay plates and the results tabulated in the table below under the heading "Antibiotic Activity (10 ml. plates)." The 10 ml. assay plates are prepared as follows: An overnight growth of the assay organism, *Staphylococcus aureus* ATCC 6538P, in nutrient broth plus 0.2% yeast extract is diluted with nutrient broth plus 0.2% yeast extract to a suspension having 40% transmittance at a wavelength of 660 mμ. This suspension is added to Difco nutrient agar supplemented with 2.0 g/l Difco yeast extract, at 47° C. to 48° C., to make a composition containing 33.2 ml. of the suspension per liter of agar. A portion (10 ml.) of this suspension is poured into petri plates of 85 mm. diameter, and the plates are chilled and held at 4° C. until used (5 day maximum).

| Age | pH | Destrose mg/ml | Antibiotic Activity vs. ATCC 6538P (mm) | Antibiotic Activity (10 ml. plates) (mm) |
| --- | --- | --- | --- | --- |
| 0 | 6.6 | 22.2 | | |
| 12 | 6.3 | 20.2 | | |
| 24 | 5.8 | 18.0 | | 0 |
| 36 | 6.0 | 13.2 | | 21.5 |
| 48 | 6.0 | 8.6 | | 21.5 |
| 60 | 5.7 | 6.4 | | 26.5 |
| 72 | 5.8 | 2.7 | | 25.5 |
| 84 | 6.2 | 0.3 | | 27.5 |
| 96 | 6.4 | 0.2 | | 36.0 |
| 108 | 6.4 | 0 | 41.5 | 35.0 |
| 120 | 6.3 | | | 37.0 |
| 132 | 5.8 | | | 37.5 |
| 144 | 5.9 | | 43.0 | 37.5 |

The 4,258 liters of fermentation broth is cooled to 15° C. and filtered using a 30 inch filter press and 204 kg. of filter aid admix. The filter press and mycelial cake are washed with sufficient cold deionized water to bring the filtered broth to the original volume. The filtered broth is cooled to 0°–5° C. and adjusted to pH 6.8–7.2. A 38 gram amount of (ethylenedinitrilo)tetraacetic acid, disodium salt is added to the filtrate. Two columns, each containing 416 L of Dowex 1×2 resin, 50–100 mesh on the bicarbonate cycle, are cooled by washing each column with 750 L of deionized water at 0°–5° C. Approximately one-half of the cooled filtered broth, adjusted to pH 7.2–7.3, is adsorbed on each column at about 45 L/min. Each column is then washed with 750 L of deionized water at 0°–5° C. at the same flow rate and eluted with carbon dioxide-saturated, dionized water at 2° C. and 23 L/min. Three fractions of 750 L, 720 L, and 190 L are collected. The second fractions of each column are combined and concentrated to 9.2 L by reverse osmosis at about 10° C. and pH 4.9–5.4.

The 9.2 L concentrate, pH 5.5–6.0, is chromatographed on 83 L of Dowex 1×2, 50–100 mesh, chloride cycle resin at 1.9 L/min. in deionized water (0°–5° C.). Eighteen fractions are collected. Fraction one is 60 L and the remainder are 8 L each. Each fraction is adjusted to pH 6.2–6.4 with concentrated ammonia and assayed. Fractions 4–10 are combined and concentrated at 10° C. to 6.5 L by reverse osmosis. The pH of the concentrate is 6.8.

Six liters of concentrate are then chromatographed on 83 L of Amberlite XAD-2, 20–50 mesh resin, precooled to 7° C. Northienamycin is eluted with deionized water (0°–5° C.) at 1.9 L/min. Sixteen fractions are collected. Fractions 1 and 16 are 79 L each and Fractions 2 through 15 are 12 L each. Fractions 5–15 are combined and further worked up to afford thienamycin.

Fraction 4 is processed, as described below, to essentially pure northienamycin. Ultraviolet and high pressure liquid chromatographic assays show Fraction 4 to contain approximately 76 mg. of northienamycin.

Five liters of Fraction 4, pH 6.4, is concentrated to 35–40 ml. and chromatographed at 5° C. on 230 ml. of finely pulverized Amberlite XAD-2 resin in cold deionized water at 3.4 ml/min. Fractions of 17 ml. each are collected. Fractions 15–20 are combined and brought with washings to 115 ml. A 110 ml. portion is further concentrated to 4 ml., filtered through a medium porosity, sintered-glass filter and freeze-dried to 0.154 g. of light tan solid, approximately 9.7% pure northienamycin by UV and HPLC (high pressure liquid chromatography, Water Associates) assay.

A 31.8 mg. sample of the lyophilized solid is dissolved in 0.75 ml. of 0.005 M potassium phosphate buffer (pH 6.8) and diluted with 0.75 ml. of acetone. The solution is chromatographed at 5° C. on 47 ml. of Sephadex G-50 (fine) resin in 1:1 acetone:0.005 M potassium phosphate buffer, pH 6.8 (v/v) at 0.27 ml/min. After a forecut of 38 ml., fractions of 2.7 ml. each are collected. Fraction purity is assexssed by evaporating 0.1 ml. at room temperature, immediately diluting with 0.1 ml. of deionized water, and assaying by HPLC, monitoring column effluent at 220 nm. Based on assays, fractions 14–24 are combined, concentrated to 15 ml. at 30° C., adjusted to pH 7.0, and further concentrated at 30° C. to 2.0 ml.

The 2.0 ml. concentrate is chromatographed at 5° C. on 25 ml. of Dowex 50×2 (K+), 200–400 mesh resin in cold deionized water at 2.6 ml/min. Fractions of 2.6 ml. each are collected and assayed by HPLC, monitoring column effluent at 300 nm. Fractions 24–34, containing 1.59 mg. of northienamycin by UV assay, are combined and concentrated at 30° C. to about 1 ml. The 1 ml. concentrate is chromatographed at 5° C. on 9.5 ml. of finely pulverized Amberlite XAD-2 in cold deionized water at 0.30 ml/min. Fractions (1.5 ml. each) are collected and assayed both by UV and by HPLC. Fractions 9–12 are combined, concentrated to about 1 ml., and freeze-dried to yield 1 mg. of essentially pure northienamycin as a fluffy white solid.

What is claimed is:

1. A process for the production of northienamycin having the structure:

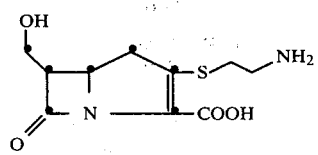

which comprises cultivating a thienamycin-producing strain of *Streptomyces cattleya* in an aqueous nutrient medium containing assimilable sources of carbohydrate, nitrogen and inorganic salts under submerged aerobic conditions and recovering the northienamycin so produced in substantially pure form.

2. The process of claim 1 wherein the organism cultivated is *Streptomyces cattleya* NRRL 8057.

* * * * *